(12) United States Patent
Stein

(10) Patent No.: US 11,679,000 B2
(45) Date of Patent: *Jun. 20, 2023

(54) EXPANDABLE FUSION IMPLANT AND RELATED METHODS

(71) Applicant: Nuvasive, Inc., San Diego, CA (US)

(72) Inventor: Christopher Stein, Fallbrook, CA (US)

(73) Assignee: NuVasive, Inc., San Diego, CA (US)

( * ) Notice: Subject to any disclaimer, the term of this patent is extended or adjusted under 35 U.S.C. 154(b) by 119 days.

This patent is subject to a terminal disclaimer.

(21) Appl. No.: 17/221,546

(22) Filed: Apr. 2, 2021

(65) Prior Publication Data

US 2021/0220145 A1    Jul. 22, 2021

Related U.S. Application Data

(63) Continuation of application No. 16/265,050, filed on Feb. 1, 2019, now abandoned, which is a continuation of application No. 15/783,977, filed on Oct. 13, 2017, now Pat. No. 10,219,915, which is a continuation of application No. 14/285,590, filed on May 22, 2014, now Pat. No. 9,788,971.

(60) Provisional application No. 61/826,299, filed on May 22, 2013.

(51) Int. Cl.
*A61F 2/44* (2006.01)
*A61F 2/30* (2006.01)
*A61F 2/46* (2006.01)

(52) U.S. Cl.
CPC .... *A61F 2/447* (2013.01); *A61F 2002/30265* (2013.01); *A61F 2002/30556* (2013.01); *A61F 2002/30579* (2013.01); *A61F 2002/30593* (2013.01); *A61F 2002/30622* (2013.01); *A61F 2002/30828* (2013.01); *A61F 2002/4627* (2013.01)

(58) Field of Classification Search
CPC ...... A61F 2/4455; A61F 2/446; A61F 2/4465; A61F 2/447
See application file for complete search history.

(56) References Cited

U.S. PATENT DOCUMENTS

| | | |
|---|---|---|
| 5,171,278 A | 12/1992 | Pisharodi |
| 5,390,683 A | 2/1995 | Pisharodi |
| 5,693,100 A | 12/1997 | Pisharodi |
| 5,782,832 A | 7/1998 | Larsen et al. |
| 6,126,689 A | 10/2000 | Brett |
| 6,174,334 B1 | 1/2001 | Suddaby |
| 6,183,517 B1 | 2/2001 | Suddaby |
| 6,332,895 B1 | 12/2001 | Suddaby |
| 6,340,369 B1 | 1/2002 | Ferree |

(Continued)

FOREIGN PATENT DOCUMENTS

| | | |
|---|---|---|
| AU | 2007202404 | 9/2016 |
| AU | 2011203582 | 9/2016 |

(Continued)

*Primary Examiner* — Si Ming Ku
(74) *Attorney, Agent, or Firm* — Hoffman Warnick LLC

(57) ABSTRACT

An expandable spinal fusion implant including first and second endplates coupled to an expansion member that sits within a housing. The expansion member is translated by a drive mechanism, whereby translation of the expansion member by the drive mechanism in a distal and proximal directions causes the distance between the endplates to increase and decrease, respectively.

18 Claims, 7 Drawing Sheets

(56) References Cited

U.S. PATENT DOCUMENTS

| | | |
|---|---|---|
| 6,344,058 B1 | 2/2002 | Ferree |
| 6,352,557 B1 | 3/2002 | Ferree |
| 6,368,351 B1 | 4/2002 | Glenn |
| 6,409,766 B1 | 6/2002 | Brett |
| 6,419,702 B1 | 7/2002 | Ferree |
| 6,488,710 B2 | 12/2002 | Besselink |
| 6,491,724 B1 | 12/2002 | Ferree |
| 6,500,205 B1 | 12/2002 | Michelson |
| 6,582,451 B1 | 6/2003 | Marucci et al. |
| 6,648,918 B2 | 11/2003 | Ferree |
| 6,652,584 B2 | 11/2003 | Michelson |
| 6,709,458 B2 | 3/2004 | Michelson |
| 6,716,247 B2 | 4/2004 | Michelson |
| 6,719,797 B1 | 4/2004 | Ferree |
| 6,743,255 B2 | 6/2004 | Ferree |
| 6,793,679 B2 | 9/2004 | Michelson |
| 6,808,537 B2 | 10/2004 | Michelson |
| 6,814,756 B1 | 11/2004 | Michelson |
| 6,962,606 B2 | 11/2005 | Michelson |
| 6,972,035 B2 | 12/2005 | Michelson |
| 6,986,772 B2 | 1/2006 | Michelson |
| 7,008,453 B1 | 3/2006 | Michelson |
| 7,044,971 B2 | 5/2006 | Suddaby |
| 7,070,598 B2 | 7/2006 | Lim et al. |
| 7,083,650 B2 | 8/2006 | Moskowitz et al. |
| 7,087,055 B2 | 8/2006 | Lim et al. |
| 7,118,579 B2 | 10/2006 | Michelson |
| 7,118,598 B2 | 10/2006 | Michelson |
| 7,547,325 B2 | 6/2009 | Biedermann et al. |
| 7,608,107 B2 | 10/2009 | Michelson |
| 7,615,052 B2 | 11/2009 | Serbousek |
| 7,621,951 B2 | 11/2009 | Glenn et al. |
| 7,625,377 B2 | 12/2009 | Veldhuizen et al. |
| 7,655,027 B2 | 2/2010 | Michelson |
| 7,678,148 B2 | 3/2010 | Peterman |
| 7,682,400 B2 | 3/2010 | Zwirkoski |
| 7,763,028 B2 | 7/2010 | Lim et al. |
| 7,763,074 B2 | 7/2010 | Altarac et al. |
| 7,846,206 B2 | 12/2010 | Oglaza et al. |
| 7,892,286 B2 | 2/2011 | Michelson |
| 7,901,409 B2 | 3/2011 | Canaveral et al. |
| 7,922,729 B2 | 4/2011 | Michelson |
| 8,007,534 B2 | 8/2011 | Michelson |
| 8,025,665 B2 | 9/2011 | Lim et al. |
| 8,075,621 B2 | 12/2011 | Michelson |
| 8,097,034 B2 | 1/2012 | Michelson |
| 8,097,035 B2 | 1/2012 | Glenn et al. |
| 8,128,662 B2 | 3/2012 | Altarac et al. |
| 8,152,837 B2 | 4/2012 | Altarac et al. |
| 8,182,538 B2 | 5/2012 | O'Neil et al. |
| 8,251,891 B2 | 8/2012 | Moskowitz et al. |
| 8,268,001 B2 | 9/2012 | Butler et al. |
| 8,303,658 B2 | 11/2012 | Peterman |
| 8,317,798 B2 | 11/2012 | Lim et al. |
| 8,328,818 B1 | 12/2012 | Seifert et al. |
| 8,377,071 B2 | 2/2013 | Lim et al. |
| 8,409,282 B2 | 4/2013 | Kim |
| 8,444,692 B2 | 5/2013 | Michelson |
| 8,496,664 B2 | 7/2013 | Michelson |
| 8,523,944 B2 | 9/2013 | Jimenez et al. |
| 8,540,452 B2 | 9/2013 | Jimenez et al. |
| 8,551,173 B2 | 10/2013 | Lechmann et al. |
| 8,579,907 B2 | 11/2013 | Lim et al. |
| 8,603,173 B2 | 12/2013 | Biedermann et al. |
| 8,628,577 B1 | 1/2014 | Jimenez |
| 8,663,329 B2 | 3/2014 | Ernst |
| 8,685,095 B2 | 4/2014 | Miller et al. |
| 8,690,917 B2 | 4/2014 | Suh et al. |
| 8,734,520 B2 | 5/2014 | Zwirkoski |
| 8,771,321 B2 | 7/2014 | Michelson |
| 8,771,358 B2 | 7/2014 | Michelson |
| 8,795,365 B2 | 8/2014 | Arcenio et al. |
| 8,795,374 B2 | 8/2014 | Chee |
| 8,828,085 B1 | 9/2014 | Jensen |
| 8,845,726 B2 | 9/2014 | Tebbe et al. |
| 8,845,730 B2 | 9/2014 | de Villiers et al. |
| 8,894,652 B2 | 11/2014 | Seifert et al. |
| 8,906,100 B2 | 12/2014 | Jimenez et al. |
| 8,940,049 B1 | 1/2015 | Jimenez et al. |
| 8,986,386 B2 | 3/2015 | Oglaza et al. |
| 8,998,992 B2 | 4/2015 | Seifert et al. |
| 9,005,291 B2 | 4/2015 | Loebl et al. |
| 9,034,040 B2 | 5/2015 | Seifert et al. |
| 9,039,742 B2 | 5/2015 | Altarac et al. |
| 9,119,726 B2 | 9/2015 | Wei |
| 9,125,692 B2 | 9/2015 | Kim |
| 9,138,327 B1 | 9/2015 | McClellan, III |
| 9,155,572 B2 | 10/2015 | Altarac et al. |
| 9,204,973 B2 | 12/2015 | Aflatoon et al. |
| 9,220,535 B2 | 12/2015 | Robling et al. |
| 9,259,328 B2 | 2/2016 | Pabst et al. |
| 9,289,308 B2 | 3/2016 | Marino et al. |
| 9,295,562 B2 | 3/2016 | Lechmann et al. |
| 9,333,093 B2 | 5/2016 | Aflatoon |
| 9,345,584 B2 | 5/2016 | Michelson |
| 9,351,846 B2 | 5/2016 | De Villiers et al. |
| 9,351,851 B2 | 5/2016 | Huffmaster et al. |
| 9,381,092 B2 | 7/2016 | Jimenez et al. |
| 9,393,130 B2 | 7/2016 | Suddaby et al. |
| 9,408,707 B2 | 8/2016 | Oglaza et al. |
| 9,408,721 B2 | 8/2016 | Eastlack et al. |
| 9,414,933 B2 | 8/2016 | Banouskou |
| 9,421,111 B2 | 8/2016 | Baynham |
| 9,433,510 B2 | 9/2016 | Lechmann et al. |
| 9,445,856 B2 | 9/2016 | Seifert et al. |
| 9,445,917 B2 | 9/2016 | Jimenez et al. |
| 9,463,099 B2 | 10/2016 | Levy et al. |
| 2003/0236520 A1 | 12/2003 | Lim et al. |
| 2005/0080422 A1 | 4/2005 | Otte et al. |
| 2005/0278036 A1 | 12/2005 | Leonard et al. |
| 2006/0004455 A1 | 1/2006 | Leonard et al. |
| 2007/0118222 A1 | 5/2007 | Lang |
| 2007/0149978 A1 | 6/2007 | Shezifi et al. |
| 2007/0282443 A1 | 12/2007 | Globerman et al. |
| 2008/0114367 A1 | 5/2008 | Meyer |
| 2008/0147193 A1* | 6/2008 | Matthis .............. A61F 2/4465 623/17.16 |
| 2009/0076607 A1 | 3/2009 | Aalsma et al. |
| 2009/0157084 A1 | 6/2009 | Aalsma et al. |
| 2009/0281628 A1 | 11/2009 | Oglaza et al. |
| 2010/0137862 A1 | 6/2010 | Diao et al. |
| 2010/0137987 A1 | 6/2010 | Diao et al. |
| 2010/0217335 A1 | 8/2010 | Chirico et al. |
| 2011/0029086 A1 | 2/2011 | Glazer et al. |
| 2011/0257748 A1 | 10/2011 | Liu |
| 2012/0101530 A1 | 4/2012 | Robling et al. |
| 2012/0290094 A1 | 11/2012 | Lim et al. |
| 2013/0023994 A1* | 1/2013 | Glerum .............. A61F 2/447 623/17.16 |
| 2013/0103154 A1 | 4/2013 | Trieu et al. |
| 2013/0116791 A1 | 5/2013 | Theofilos |
| 2013/0144388 A1 | 6/2013 | Emery et al. |
| 2013/0190876 A1 | 7/2013 | Drochner et al. |
| 2013/0297029 A1 | 11/2013 | Kana et al. |
| 2013/0304213 A1 | 11/2013 | Aflatoon et al. |
| 2014/0018922 A1 | 1/2014 | Marino et al. |
| 2014/0031940 A1 | 1/2014 | Banouskou |
| 2014/0039625 A1 | 2/2014 | To et al. |
| 2014/0114420 A1 | 4/2014 | Robinson |
| 2014/0135776 A1 | 5/2014 | Huffmaster et al. |
| 2014/0148904 A1 | 5/2014 | Robinson |
| 2014/0156007 A1 | 6/2014 | Pabst et al. |
| 2014/0163682 A1 | 6/2014 | Lott et al. |
| 2014/0163683 A1 | 6/2014 | Seifert et al. |
| 2014/0180419 A1 | 6/2014 | Dmuschewsky |
| 2014/0236296 A1 | 8/2014 | Wagner et al. |
| 2014/0243983 A1 | 8/2014 | Galea et al. |
| 2014/0277139 A1 | 9/2014 | Vrionis et al. |
| 2014/0277492 A1 | 9/2014 | Wei |
| 2014/0277498 A1 | 9/2014 | Ainsworth et al. |
| 2014/0277499 A1 | 9/2014 | Ainsworth et al. |
| 2014/0277508 A1 | 9/2014 | Baynham |
| 2014/0296984 A1 | 10/2014 | Etminan |
| 2014/0309741 A1 | 10/2014 | Ganter et al. |

(56) References Cited

U.S. PATENT DOCUMENTS

| | | |
|---|---|---|
| 2014/0343677 A1 | 11/2014 | Davis et al. |
| 2014/0343678 A1 | 11/2014 | Suddaby et al. |
| 2014/0358246 A1 | 12/2014 | Levy et al. |
| 2014/0364951 A1 | 12/2014 | De Villiers et al. |
| 2015/0012098 A1 | 1/2015 | Eastlack et al. |
| 2015/0112437 A1 | 4/2015 | Davis et al. |
| 2015/0182347 A1 | 7/2015 | Robinson |
| 2015/0230935 A1 | 8/2015 | Aflatoon |
| 2015/0238230 A1 | 8/2015 | Suh et al. |
| 2015/0342586 A1 | 12/2015 | Lim et al. |
| 2016/0022434 A1 | 1/2016 | Robinson |
| 2016/0022438 A1 | 1/2016 | Lamborne et al. |
| 2016/0030190 A1 | 2/2016 | Robinson |
| 2016/0067056 A1 | 3/2016 | Armstrong et al. |
| 2016/0074174 A1 | 3/2016 | Halverson et al. |
| 2016/0081724 A1 | 3/2016 | Robling et al. |
| 2016/0089247 A1 | 3/2016 | Nichols et al. |
| 2016/0242927 A1 | 8/2016 | Seifert et al. |
| 2016/0250034 A1 | 9/2016 | Loebl et al. |
| 2016/0256148 A1 | 9/2016 | Huffmaster et al. |

FOREIGN PATENT DOCUMENTS

| | | |
|---|---|---|
| CN | 101502436 | 9/2016 |
| CN | 104248465 | 9/2016 |
| CN | 105232191 | 9/2016 |
| CN | 202568534 | 9/2016 |
| CN | 203183090 | 9/2016 |
| CN | 204306881 | 9/2016 |
| CN | 204931904 | 9/2016 |
| DE | 20314708 | 11/2003 |
| DE | 10344019 | 9/2016 |
| EP | 2777633 | 11/2003 |
| FR | 2717068 | 11/2003 |
| FR | 2813519 | 11/2003 |
| FR | 3006169 | 11/2003 |
| JP | 2008054710 | 11/2003 |
| JP | 2014073405 | 11/2003 |
| JP | 2016013460 | 11/2003 |
| KR | 100395252 | 11/2003 |
| KR | 20020084349 | 11/2003 |
| RU | 2070006 | 11/2003 |
| WO | WO200103616 | 11/2003 |
| WO | WO2005006944 | 11/2003 |
| WO | WO2006042334 | 11/2003 |
| WO | WO2007038349 | 11/2003 |
| WO | WO2007070024 | 11/2003 |
| WO | WO9214423 | 4/2008 |
| WO | WO9525485 | 4/2008 |
| WO | WO2008044057 | 4/2008 |
| WO | WO2010078468 | 4/2008 |
| WO | WO2012089317 | 4/2008 |
| WO | WO2014091028 | 4/2008 |
| WO | WO2014144696 | 4/2008 |
| WO | WO2014186384 | 4/2008 |
| WO | WO2015063719 | 4/2008 |
| WO | WO2015063721 | 4/2008 |
| WO | WO2015097416 | 4/2008 |
| WO | WO2015198335 | 4/2008 |
| WO | WO2016040125 | 4/2008 |

\* cited by examiner

EXPANDABLE FUSION IMPLANT AND RELATED METHODS

CROSS REFERENCE TO RELATED APPLICATIONS

This application is a continuation of U.S. patent application Ser. No. 15/783,977 filed on Oct. 13, 2017, which is a continuation of U.S. patent application Ser. No. 14/285,590 filed on May 22, 2014, which claims priority from U.S. Provisional Application Ser. No. 61/826,299 filed on May 22, 2013, entitled "Expandable Spinal Fusion Implant and Related Methods," the contents of all of which are incorporated herein by reference in their entirety.

BACKGROUND

This application relates to an expandable spinal fusion implant for use in spinal surgery.

SUMMARY

To reduce risk of neural injury, the device will have the ability to be implanted to an intervertebral disc space in a collapsed state and expanded to a desired height. Expansion will be accomplished by translating an expansion mechanism mated to the inferior and superior endplates. In addition a large aperture at the proximal end of the device allows for post packing of bone graft material into the hollow interior of the device, which is in communication with a fusion aperture in each of the superior and inferior endplates. In order to have the large through aperture at the proximal end of the device, the drive mechanism is offset from the width centerline of the device.

The device includes a housing, expansion mechanism, support rails, superior endplate, inferior endplate, endplate retainer, endplate safety retainer, drive mechanism, and drive mechanism retainer.

The expansion mechanism rides on rails that are retained partially in both the housing and expansion mechanism. There is one rail on each of the two lateral sides of the device. The expansion mechanism has ramps that are on the superior and inferior sides at both the distal and proximal ends. The ramps on the superior side mate with the superior endplate and the ramps on the inferior side mate with the inferior endplate. The expansion member includes a hollow interior for receiving bone graft material and for allowing bone growth therethrough. The hollow interior of the expansion mechanism is in communication with fusion apertures in each of the superior and inferior endplates.

To achieve expansion and contraction the endplates must be fixed in the longitudinal direction during translation of the expansion mechanism. An endplate retainer housed within the distal end of the housing mates with both the superior and inferior endplates and prohibits translation of the endplates, but allows for expansion.

The expansion mechanism is translated by advancing the drive mechanism, which is retained within the proximal end of the housing and offset from the width centerline. This offset allows for the large through cannula and post packing of bone graft material. The drive mechanism is mated to the expansion mechanism with the drive mechanism retainer. Advancement of the drive mechanism toward the distal end of the device allows the endplates to expand, while the withdrawal of the drive mechanism toward the proximal end of the device results in contraction of the endplates.

An endplate safety retainer located in the expansion mechanism prohibits the removal of the superior and inferior endplates from the expansion mechanism. Superior and inferior in flat and lordotic configurations are contemplated for use with the device described herein.

DETAILED DESCRIPTION

Figure 1:
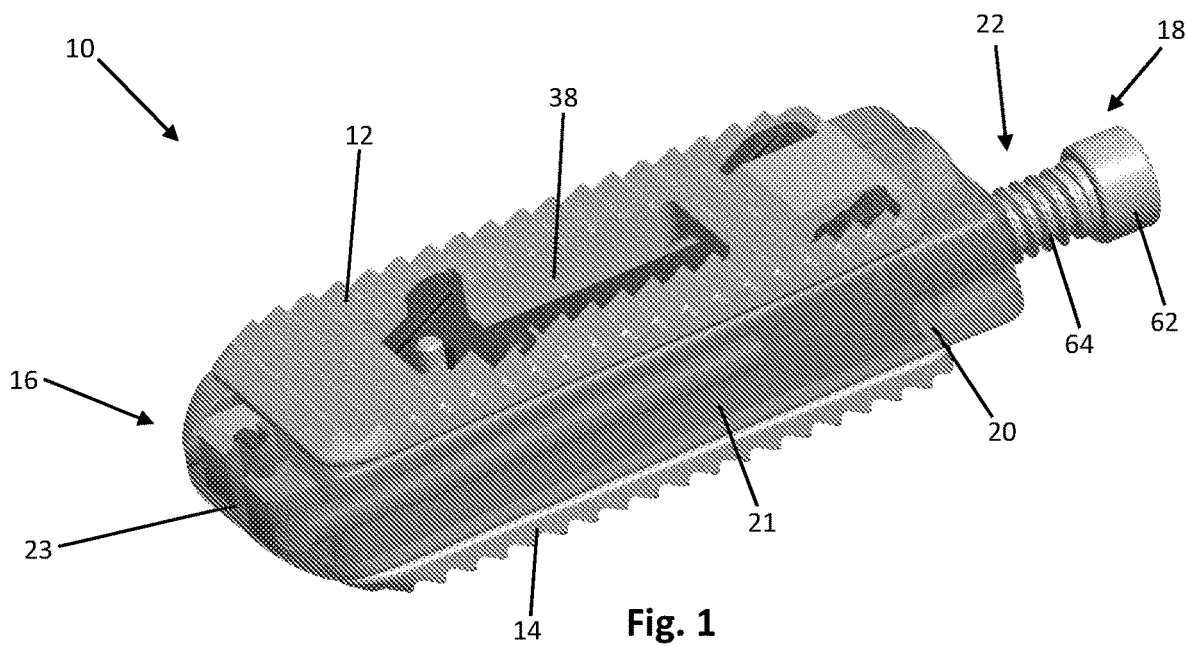
FIG. 1 is a perspective view of an exemplary embodiment of an expandable spinal fusion implant in its collapsed state.
Figure 2:
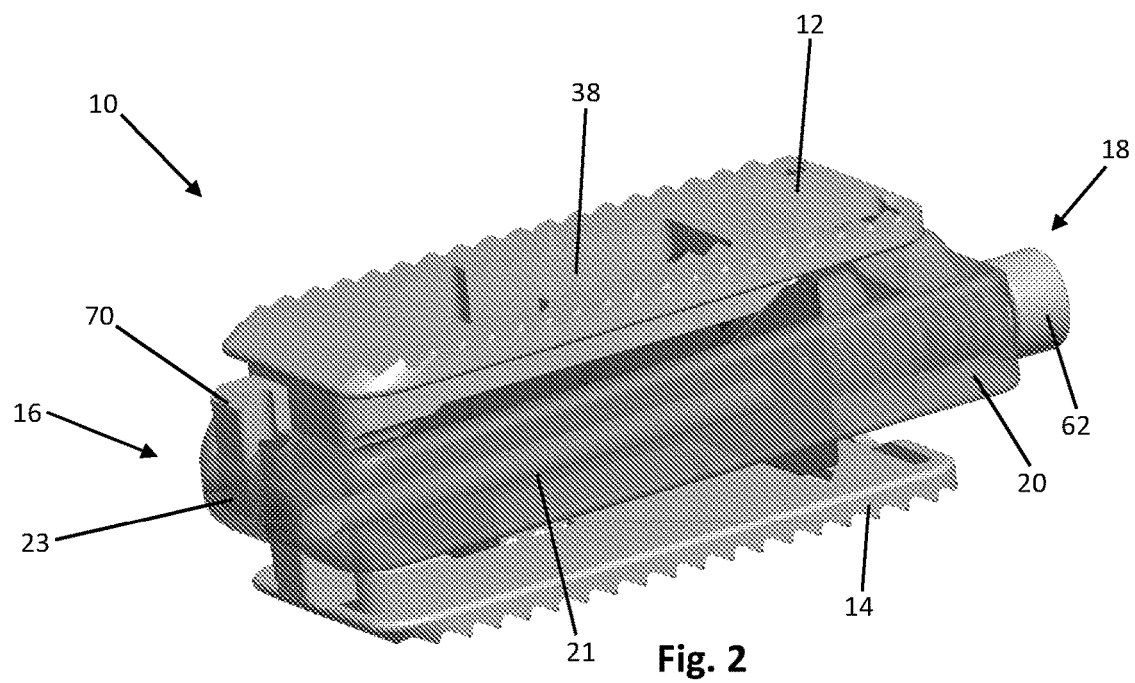
FIG. 2 is a perspective view of the expandable spinal fusion implant of FIG. 1 in its expanded state.
Figure 3:
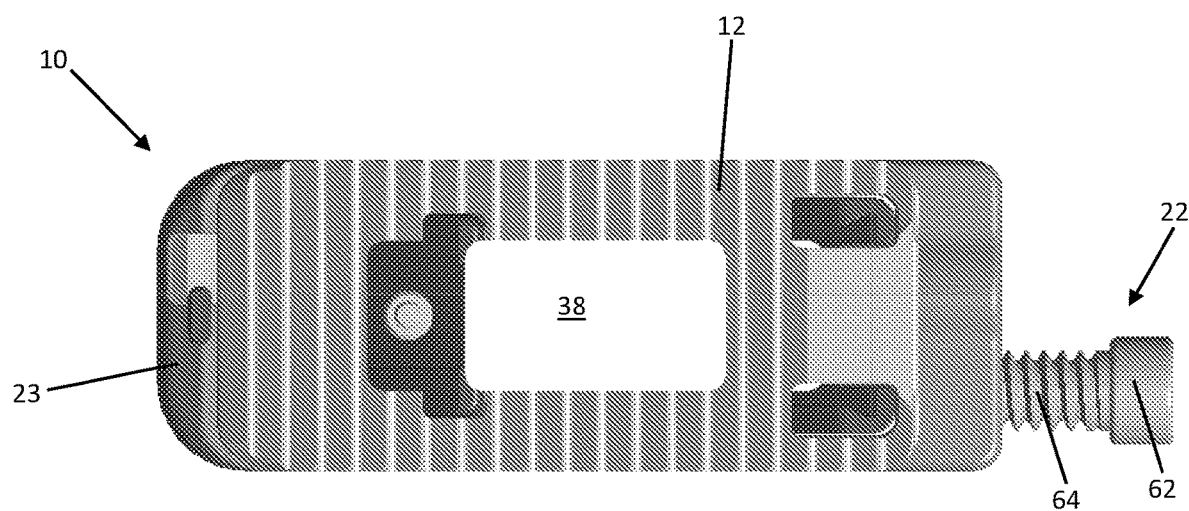
FIG. 3 is a top view of the expandable spinal fusion implant of FIG. 1.
Figure 4:
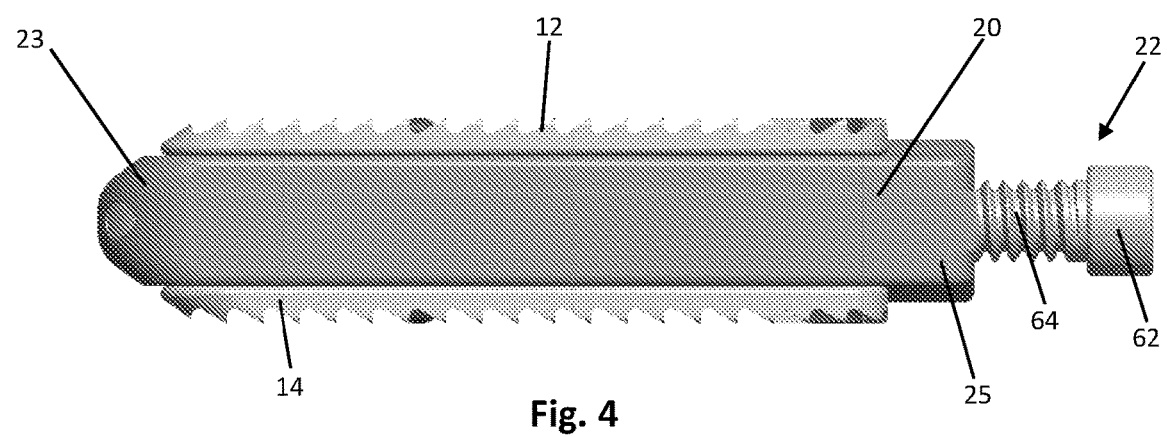
FIG. 4 is a side view of the expandable spinal fusion implant of FIG. 1 in its collapsed state.
Figure 5:
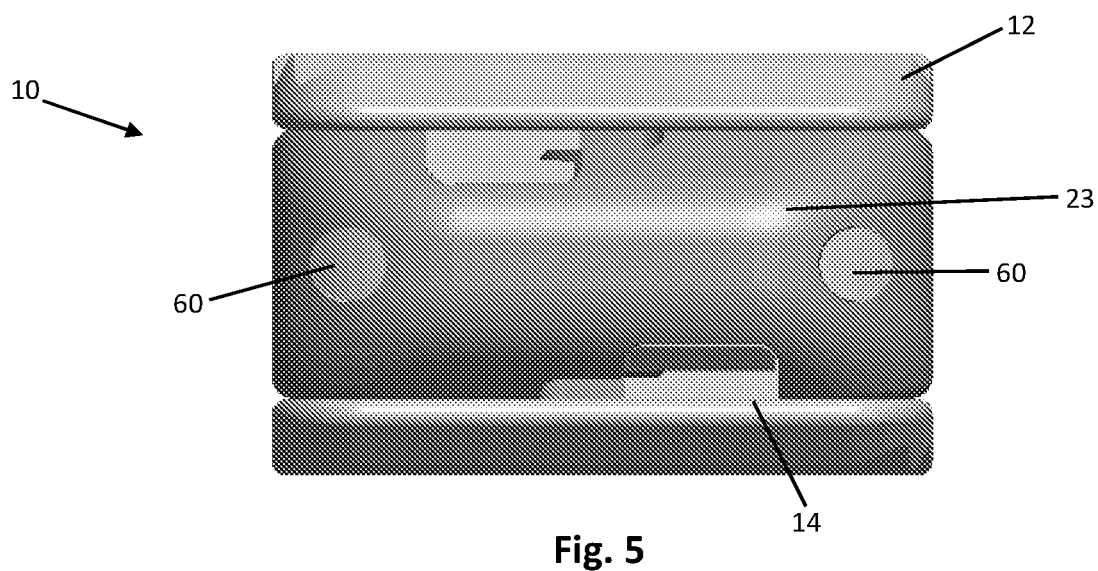
FIG. 5 is a leading end view of the expandable spinal fusion implant of FIG. 1 in its collapsed state.

FIGS. 1-13 illustrate an expandable spinal fusion implant for use during spinal surgery for implantation to an intervertebral disc space. According to an exemplary embodiment, the device is dimensioned for posterior approach surgery, e.g. posterior lumber interbody fusion (PLIF) and transforaminal lumbar interbody fusion (TLIF) approaches. However, according to an alternative embodiment, the device may also be dimensioned for use in a lateral approach to the anterior column of the spine. To reduce the risk of neural injury, the expandable spinal fusion implant has the ability to be implanted in a collapsed state (see FIG. 1) and expand to a height determined by the user (see FIG. 2). Expansion is accomplished by translating a wedge shaped expansion mechanism that is mated to the inferior and superior endplates 14, 12. As the expansion mechanism 26 is advanced towards the distal or leading end 16 of the implant 10 the endplates expand in height. To reduce the height of the implant or return the endplates back to their start position the expansion mechanism is advanced towards the proximal end of the device. In addition a large cannula at the trailing or proximal end of the device allows for post packing of bone graft material, i.e. filling the interior of the device with bone graft after the device has been inserted into the intervertebral space and expanded to the desired height. The ability to post pack improves the chances of a successful surgical outcome by allowing for insertion of a sufficient amount of bone graft in adequate contact with the vertebral body endplates adjacent the disc space to promote bone growth.

As shown in FIGS. 1-13, the expandable spinal fusion implant 10 has a top endplate 12 and a bottom endplate 14.

The endplates 12, 14 have substantially identical features as will be further described. Each endplate has a bone contacting surface 46 and an interior surface 48. As shown in the exemplary embodiment, the bone contacting surfaces 46 may have anti-migration features 44. The interior surfaces 48 of the endplates 12, 14 have ramped portions 36 that correspond to the angles of the ramps 34, 35 on the expansion mechanism 26. The ramped portions 36 of the interior endplates also include a male dovetail feature 40 that mates with the female dovetail feature 38 on the ramps 34 of the expansion mechanism 26. Each endplate 12, 14 has a central fusion aperture 38 to allow for bone growth through the implant 10 and with the endplates of the adjacent vertebral bodies. In order for each endplate 12, 14 to expand it must remain stationary in the longitudinal axis as the expansion mechanism 26 translates both proximally and distally. Both endplates 12, 14 further include a distal extension 70 to aid in retaining the endplates within the housing 20. While the implant 10 according to an exemplary embodiment in FIGS. 1-13 is shown with flat endplates, endplates having built in lordosis, i.e. having a distal height extending from the bone contacting surface to the interior surface that is greater than the proximal height, are also contemplated.

The expandable spinal fusion implant 10 includes an expansion mechanism 26 located between the top and bottom endplates 12, 14. The expansion mechanism has two wedge portions 50, each of which as a superior ramp 34 and an inferior ramp 35 that correspond to and mate with the ramped portions 36, 37 of the superior and inferior endplates, respectively. Each endplate 12, 14 mates to the expansion mechanism 26 by an undercut or dovetail connection, at both the proximal end and the distal end, that allows movement between the wedge 50 and the endplate 12, 14. Each of the superior ramps 34 and inferior ramps 35 include a female dovetail feature 38 that mates with the male dovetail features 36 on the endplates 12, 14. An endplate safety retainer is housed within the expansion mechanism to prohibit removal of the endplates once assembled. The expansion mechanism 26 has a recess 56 at its proximal end dimensioned to receive the drive mechanism retainer 24 therein. The expansion mechanism 26 has a hollow interior defining a central fusion aperture 39 that aligns with the central fusion aperture 38 of the top and bottom endplates 12, 14 to allow for bone growth therethrough. The distal wedge 50 of the expansion mechanism 26 includes an endplate safety retainer 32 extending therethrough to prevent the dislocation of the endplates 12, 14 from the expansion mechanism 26.

Figure 6:
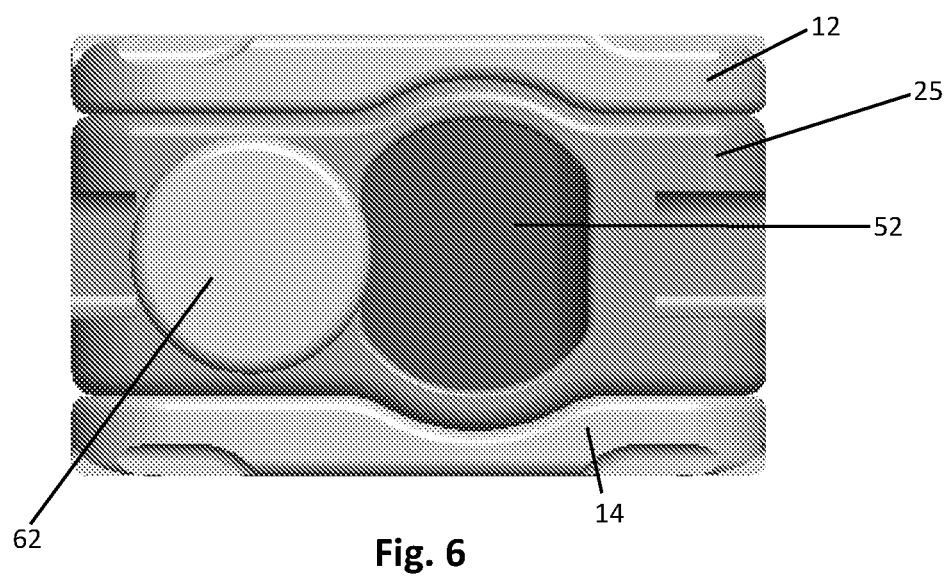
FIG. 6 is a trailing end view of the expandable spinal fusion implant of FIG. 1 in its collapsed state.
Figure 7:
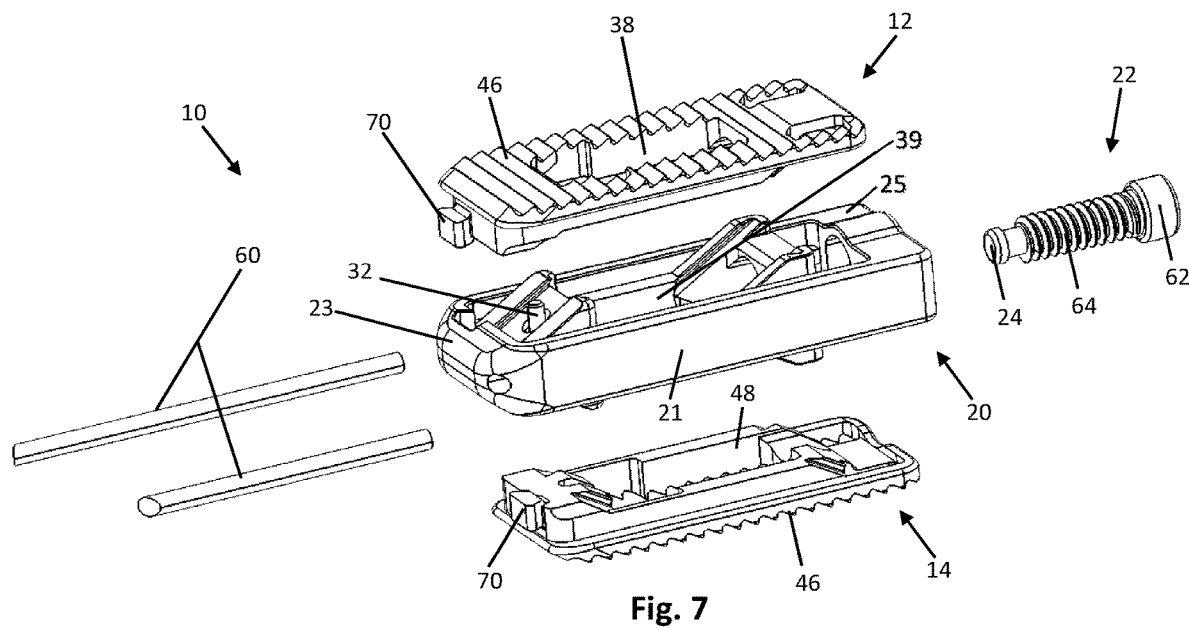
FIG. 7 is an exploded view of the expandable spinal fusion implant.
Figure 8:
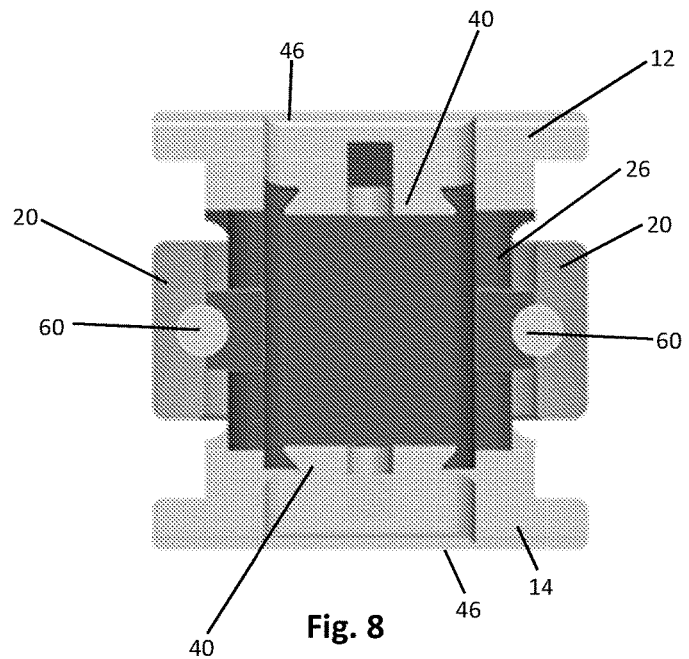
FIG. 8 is a cross sectional view of the leading end of expandable spinal fusion implant in its expanded state.
Figure 9:
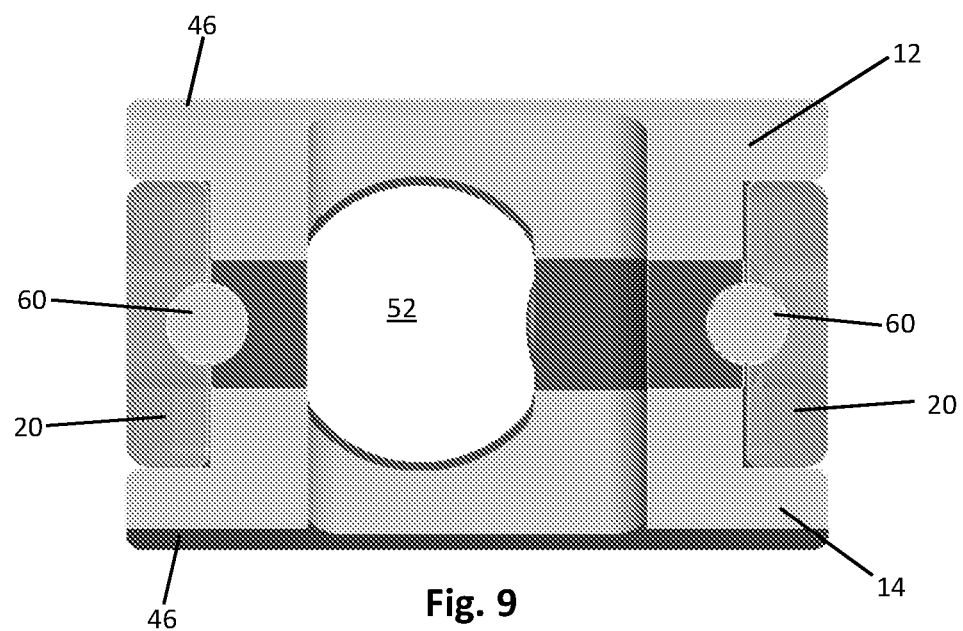
FIG. 9 is a cross sectional view of the trailing end of the expandable spinal fusion implant in its collapsed state.
Figure 10:
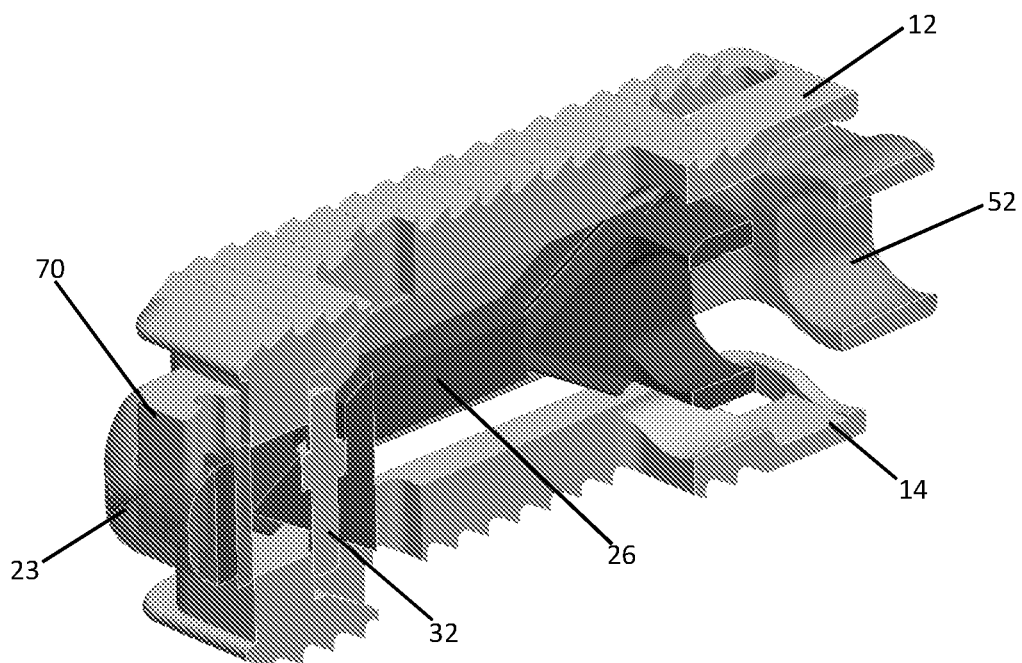
FIG. 10 is a cross sectional view of the expandable spinal fusion implant.
Figure 11:
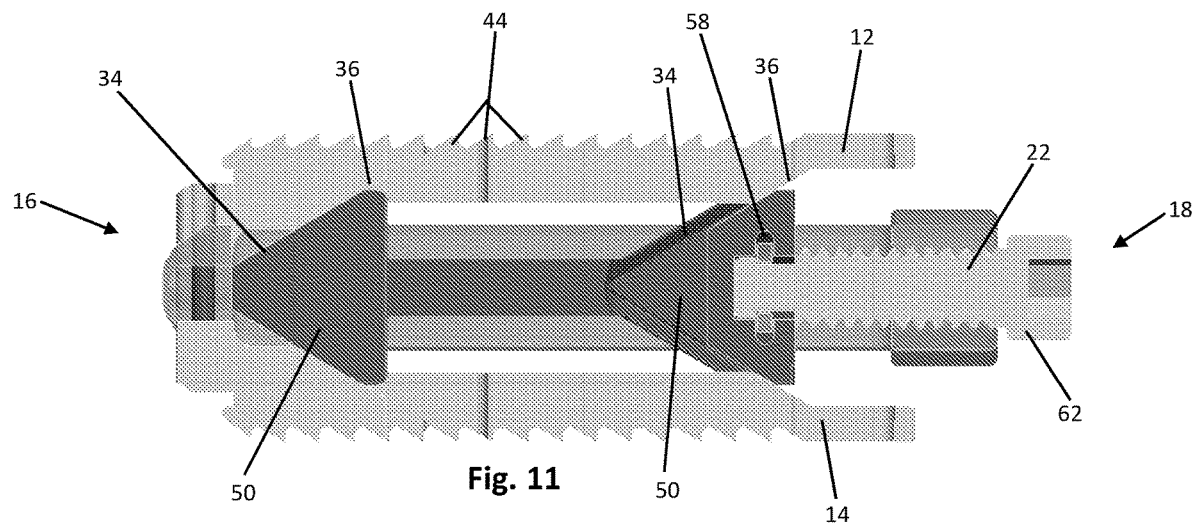
FIG. 11 is a cross sectional view of the expandable spinal fusion implant.
Figure 12:
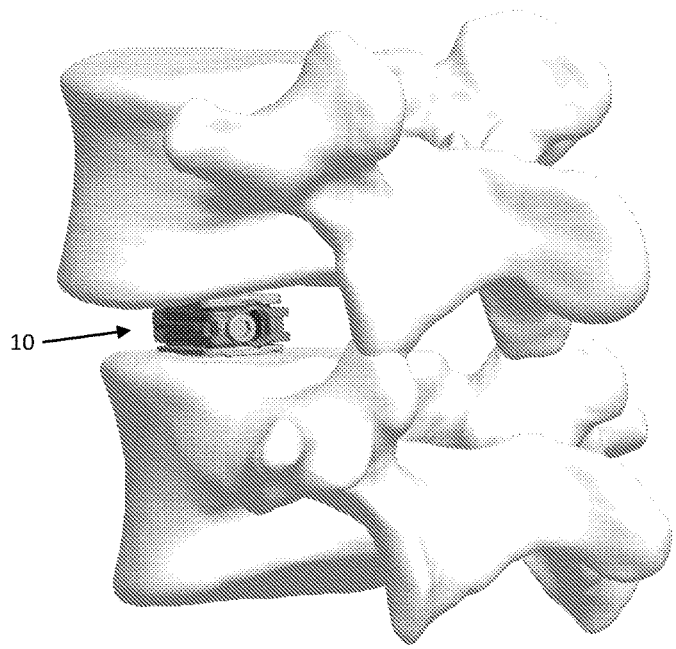
FIG. 12 is a perspective view of the expandable spinal fusion implant after insertion into the disc space.
Figure 13:
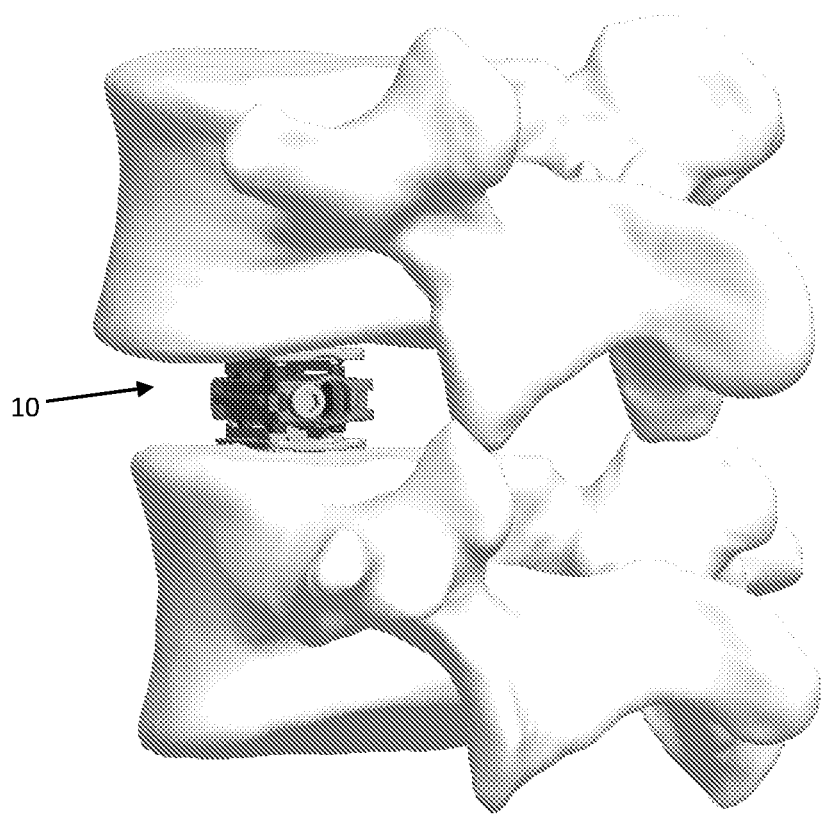
FIG. 13 is a perspective view of the expandable spinal fusion implant in its fully expanded state in the disc space.

As best shown in FIG. 7, the expandable spinal fusion implant 10 also includes a housing 20 dimensioned to house the expansion mechanism 26. The expansion mechanism 26 is supported in the housing 20 by two support rails 60. The housing 20 is defined by opposing lateral walls 21, a distal wall 23 and a proximal wall 25. The housing 20 has a longitudinal length that exceeds the longitudinal length of the endplates 12, 14. The distal wall 23 of the housing is tapered to aid in insertion of the implant 10. The distal wall 23 also includes recesses 58 for receiving the distal extensions 50 of the endplates 12, 14 to retain the endplates within in the housing 20. As seen in FIG. 6, the proximal wall 25 of the housing 20 includes a cannula 52 for receiving bone graft material into the central fusion aperture 39 of the expansion mechanism 26 as well as a threaded drive mechanism aperture 54 for receiving the drive mechanism 22 therethrough.

According to the exemplary embodiment, the drive mechanism 22 has a head 62 at its proximal end for engaging an actuator tool (not shown) and a threaded shaft 64 extending from the head 62 and terminating at the distal end with a drive mechanism retainer 24 configured to anchor the drive mechanism 22 to the expansion mechanism 26. The purpose of the drive mechanism 22 is to translate the expansion mechanism 26 both proximally and distally. The threaded shaft 64 of the drive mechanism 22 engages with the threaded aperture 54 of the housing 20 at the proximal end 25 and also mates with the recess 56 at the proximal end of the expansion mechanism 26 and is retained with the expansion mechanism 26 by a drive mechanism retainer 24. As best seen in FIG. 6, the drive mechanism 22 is located at a position within the implant 10 that is offset from the central longitudinal axis of the implant 10 to allow for post packing of bone graft through the cannula 52 and into the central fusion aperture 39.

According to the exemplary embodiment, the expandable spinal fusion implant 10 is implanted into a patient by first accessing the desired intervertebral disc space via lateral approach to the anterior spinal column or a posterior (e.g. PLIF or TLIF) approach. The implant 10 is inserted in its collapsed state into the intervertebral disc space and maneuvered into a desired position. Once the desired position is reached, a tool is engaged with the drive mechanism 22 to turn the drive mechanism 22 and thereby urge the expansion mechanism 26 in the distal direction and consequently increase the distance between the top and bottom endplates 12, 14. The drive mechanism 22 can then be turned in the opposite direction to urge the expansion mechanism 26 in the proximal direction in order to decrease the distance between the endplates 12, 14 if necessary. Once the implant 10 has been set at the desired height, bone graft can be introduced through the cannula 52 in the proximal end 25 of the housing 20 to the interior of the implant 10, into the central fusion apertures 38, 39 of the expansion mechanism 26 and endplates 12, 14.

What is claimed is:

1. An expandable fusion implant, comprising:
    first and second endplates each having a bone contacting surface;
    a housing;
    an expansion mechanism configured to translate on a plurality of rails at least partially disposed within the housing; and
    a drive mechanism having a head, a shaft extending from the head and terminating in a distal end, the shaft dimensioned to be received through an aperture in a proximal wall of the housing and the distal end configured to be received within a recess in the expansion mechanism,
    wherein the drive mechanism is configured to translate the expansion mechanism relative to a distal wall of the housing, and the expansion mechanism is configured to change a distance between the first and second endplates, and
    wherein an entirety of the drive mechanism extends along a single longitudinal axis that is offset from a central longitudinal axis extending between the proximal wall and the distal wall of the housing.

2. The expandable fusion implant of claim 1, wherein the first and second endplates comprise an inferior endplate and a superior endplate.

3. The expandable fusion implant of claim 1, having a fusion aperture extending between the bone contact surfaces of the first and second endplates.

4. The expandable fusion implant of claim 3, wherein a central aperture in the expansion mechanism is in communication with the fusion aperture.

5. The expandable fusion implant of claim 1, wherein rotation of the shaft in a first direction translates the expansion mechanism toward the distal wall of the housing, the expansion mechanism configured to move the endplates relative to the housing and increase the distance between the endplates.

6. The expandable fusion implant of claim 5, wherein rotation of the shaft in a second direction opposite the first direction, translates the expansion mechanism away from the distal wall of the housing, the expansion mechanism configured to move the endplates relative to the housing and decrease the distance between the endplates.

7. An expandable fusion implant, comprising:
first and second endplates each having a bone contacting surface and an interior surface, the interior surface of each of the first and second endplates including a first and second ramped portions;
an expansion mechanism having a first wedge and a second wedge that engage the first and second ramped portions of the first endplate and the first and second ramped portions of the second endplate;
a housing defined by opposing lateral walls, a distal wall and a proximal wall, the housing having at least one rail retained at least partially in the housing with the expansion mechanism configured to ride on the at least one rail; and
a drive mechanism having a head, a shaft extending from the head and terminating in a distal end, the shaft dimensioned to be received through an aperture in the proximal wall of the housing and the distal end configured to be received within a recess in the expansion mechanism,
wherein rotation of the shaft in a first direction translates the expansion mechanism toward the distal wall of the housing, the expansion mechanism configured to move the endplates relative to the housing to increase the distance between the endplates, and
wherein a central axis of an entirety of the drive mechanism is offset from a central axis of the housing extending from the proximal wall to the distal wall of the housing.

8. The expandable fusion implant of claim 7, wherein rotation of the shaft in a second direction opposite the first direction, translates the expansion mechanism away from the distal wall of the housing, the expansion mechanism configured to move the endplates relative to the housing and decrease the distance between the endplates.

9. The expandable fusion implant of claim 7, having a fusion aperture extending between the bone contact surfaces of the first and second endplates.

10. The expandable fusion implant of claim 7, wherein each of the first and second endplates includes a distal extension projecting from a distal end thereof towards the distal wall of the housing.

11. The expandable fusion implant of claim 7, wherein the first wedge includes a first ramp and the second wedge includes a second ramp, and each of the first and second ramps of the first and second wedges face at least partially toward the distal wall of the housing.

12. The expandable fusion implant of claim 7, wherein the first wedge engages the first ramped surfaces of the first endplate and the second endplate when the expansion mechanism translates toward the distal wall of the housing, and the second wedge engages the second ramped surfaces of the first endplate and the second endplate when the expansion mechanism translates toward the distal wall of the housing.

13. An expandable fusion implant, comprising:
first and second endplates each having a bone contacting surface and an interior surface with a central fusion aperture extending there between, the interior surface of each of the first and second endplates including a first and second ramped portions;
an expansion mechanism having a first wedge and a second wedge that engage the first and second ramped portions of the first endplate and the first and second ramped portions of the second endplate;
a housing defined by opposing lateral walls, a distal wall and a proximal wall, the housing having at least one rail retained at least partially in the housing with the expansion mechanism configured to ride on the at least one rail; and
a drive mechanism having a head, a shaft extending from the head and terminating in a distal end, the shaft dimensioned to be received through an aperture in the proximal wall of the housing and the distal end configured to the received within a recess in the expansion mechanism;
wherein rotation of the shaft translates the expansion mechanism relative to the distal wall of the housing, and
wherein a central axis of an entirety of the drive mechanism is offset from a central axis of the housing extending from the proximal wall to the distal wall of the housing.

14. The expandable fusion implant of claim 13, wherein rotation of the shaft in a first direction translates the expansion mechanism toward the distal wall of the housing, the expansion mechanism configured to move the endplates relative to the housing and increase the distance between the endplates.

15. The expandable fusion implant of claim 13, wherein rotation of the shaft in a second direction opposite the first direction, translates the expansion mechanism away from the distal wall of the housing, the expansion mechanism configured to move the endplates relative to the housing and decrease the distance between the endplates.

16. The expandable fusion implant of claim 13, wherein the drive mechanism is offset from a width centerline extending from the proximal wall to the distal wall of the housing.

17. The expandable fusion implant of claim 13, wherein each of the first and second endplates includes a distal extension projecting from a distal end thereof towards the distal wall of the housing.

18. The expandable fusion implant of claim 13, wherein the first wedge engages the first ramped surfaces of the first endplate and the second endplate when the expansion mechanism translates toward the distal wall of the housing, and the second wedge engages the second ramped surfaces of the first endplate and the second endplate when the expansion mechanism translates toward the distal wall of the housing.

\* \* \* \* \*